Figure 1:
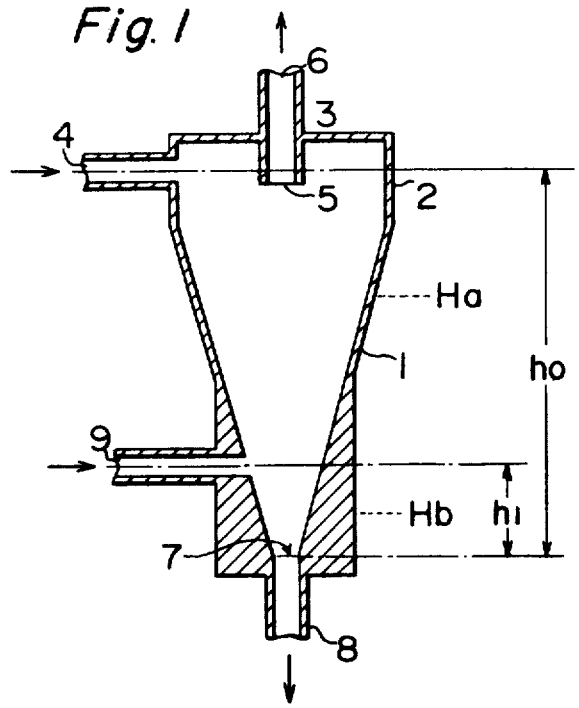

United States Patent [19]

Shiraki

[11] 4,212,995

[45] Jul. 15, 1980

[54] PROCESS FOR TREATMENT BY LIQUID CYCLONE FOR PRODUCTION OF TEREPHTHALIC ACID SUSPENSION HAVING REDUCED IMPURITY CONTENT

[75] Inventor: Shigemi Shiraki, Iwakuni, Japan

[73] Assignee: Mitsui Petrochemical Industries Ltd., Tokyo, Japan

[21] Appl. No.: 931,891

[22] Filed: Aug. 8, 1978

[30] Foreign Application Priority Data

Aug. 12, 1977 [JP] Japan .................................. 52-96176

[51] Int. Cl.$^2$ ............................................ C07C 51/42
[52] U.S. Cl. ................................................. 562/485
[58] Field of Search .......................................... 562/485

[56] References Cited

U.S. PATENT DOCUMENTS 3,853,924 12/1974 Meyer et al. ......................... 562/485

FOREIGN PATENT DOCUMENTS 970492 9/1964 United Kingdom .

*Primary Examiner*—Alan Siegel
*Attorney, Agent, or Firm*—Sherman & Shalloway

[57] ABSTRACT

A process for treatment by a liquid cyclone for the production of a suspension of terephthalic acid having a reduced impurity content which comprises supplying a fresh and hot lower aliphatic carboxylic acid solvent to a liquid-phase catalytic oxidation product of a p-alkylbenzene or a hot, impurity-containing suspension of terephthalic acid particles in a mother liquor containing a lower aliphatic carboxylic acid solvent, feeding the resulting mixture into a liquid cyclone, treating it in the cyclone at an elevated temperature, withdrawing an impurity-containing liquid composed mainly of said mother liquor from a withdrawal opening provided near one end of the cyclone, and withdrawing a suspension of terephthalic acid particles in a lower aliphatic carboxylic acid solvent consisting mainly of said fresh solvent from a withdrawal opening provided near the other end of the cyclone; wherein a fresh lower aliphatic carboxylic acid solvent is additionally supplied into the cyclone through an opening provided between a position apart from the suspension withdrawal opening of the liquid cyclone toward its mixture-feeding opening by a distance corresponding to about two-thirds of the distance ($h_o$) from the mixture-feeding opening to the suspension withdrawal opening and a position apart from the suspension withdrawal opening toward its mixture feeding opening by a distance corresponding to about one-tenth of the distance ($h_o$).

5 Claims, 2 Drawing Figures

PROCESS FOR TREATMENT BY LIQUID CYCLONE FOR PRODUCTION OF TEREPHTHALIC ACID SUSPENSION HAVING REDUCED IMPURITY CONTENT

This invention relates to an improved method for producing a terephthalic acid suspension having a reduced impurity content by treating a liquid-phase catalytic oxidation product of a p-alkylbenzene or a hot impurity-containing suspension of terephthalic acid particles in a mother liquor containing a lower aliphatic carboxylic acid solvent which is derived from the oxidation product. It provides an improved process which can give by an easy operation and a simple apparatus a terephthalic acid suspension having decreased amounts of impurities, for example oxidation intermediates such as 4-carboxybenzaldehyde, colored substances and oxidation catalyst.

More specifically, the invention relates to a process for treatment by a liquid cyclone for the production of a suspension of terephthalic acid having a reduced impurity content which comprises supplying a fresh and hot lower aliphatic carboxylic acid solvent to a liquid-phase catalytic oxidation product of a p-alkylbenzene or a hot, impurity-containing suspension of terephthalic acid particles in a mother liquor containing a lower aliphatic carboxylic acid solvent, feeding the resultant mixture into a liquid cyclone, treating it in the cyclone at an elevated temperature, withdrawing an impurity-containing liquid composed mainly of said mother liquor from a withdrawal opening provided near one end of the cyclone, and withdrawing a suspension of terephthalic acid particles in a lower aliphatic carboxylic acid solvent consisting mainly of said fresh solvent from a withdrawal opening provided near the other end of the cyclone; wherein a fresh lower aliphatic carboxylic acid solvent is additionally supplied into the cyclone through an opening provided between a position apart from the suspension withdrawal opening of the liquid cyclone toward its mixture-feeding opening by a distance corresponding to about two-thirds of the distance ($h_o$) from the mixture-feeding opening to the suspension withdrawal opening and a position apart from the suspension withdrawl opening toward its mixture-feeding opening by a distance corresponding to about one-tenth of the distance ($h_o$).

Terephthalic acid is generally produced by oxidizing a p-alkylbenzene such as p-xylene in the liquid phase with a molecular oxygen-containing gas such as air in a lower aliphatic carboxylic acid solvent in the presence of a heavy metal-containing oxidation catalyst such as a catalyst comprising cobalt and manganese at an elevated temperature and an elevated pressure. It is the widespread practice to subject the resulting crude terephthalic acid-containing oxidation product to various purifying treatments, such as hydrogenation, decarbonylation, oxidation, recrystallization and high-temperature dipping, in the presence of a solvent having a low dissolving power for terephthalic acid, such as a lower aliphatic carboxylic acid (e.g., acetic acid or propionic acid), water, or a mixture of both, or a ketone (e.g., acetone or methyl ethyl ketone).

The oxidation product or the purified product is obtained as an impurity-containing suspension of terephthalic acid particles in a mother liquor containing a lower aliphatic carboxylic acid solvent because terephthalic acid is only slightly soluble in the above solvent and impurities in the product cannot be fully removed by the aforesaid purifying treatments.

Solid-liquid separating means, such as centrifugal separation, are most widely employed to separate such a liquid-phase catalytic oxidation product of a paraalkylbenzene or the impurity-containing suspension of terephthalic acid particles in the solvent-containing mother liquor which is derived from the oxidation product, into the mother liquor and terephtalic acid particles.

Recovery of good purity terephthalic acid crystals from the suspension by a centrifugal separating means, however, suffers from operational disadvantages. For example, the mother liquor containing the lower aliphatic carboxylic acid solvent is corrosive on metallic materials, especially at elevated temperatures. Corrosion may be prevented by flushing the mother liquor to a space under atmospheric pressure and cooling it. In this case, however, when that portion of terephthalic acid which is dissolved in the suspension is precipitated, impurities precipitate simultaneously or are occluded in the crystallized terephthalic acid.

Usually, therefore, the hot impurity-containing suspension of terephthalic acid particles in the solvent-containing mother liquor is first cooled to a temperature below the boiling point of the solvent contained in it, and then centrifuged to separate it into the terephthalic acid particles and the mother liquor. Impurities such as the catalyst, oxidation intermediates and colored substance contained in the suspension are dissolved in the solvent while the suspension is still hot. However, when the suspension is cooled to a temperature below the boiling point of the solvent at atmospheric pressure, these impurities precipitate together with that part of terephthalic acid which is dissolved, and contaminate the terephthalic acid crystals or are occluded in them. Consequently, the quality of the separated terephthalic acid is reduced.

When in an attempt to avoid the above troubles, the suspension is centrifugally separated in the hot state, the corrosion of metallic materials by the mother liquor increases remarkably. Hence, an expensive metallic material such as titanium must be employed to build the centrifugal separator. Furthermore, since at high temperatures, the vapor pressure of the lower aliphatic carboxylic acid solvent is also high, the centrifugal separator must have high pressure resistance. In practice, it is extremely difficult both technically and economically to build a centrifugal separator which is feasible under such high-temperature high-pressure conditions without involving these troubles. Accordingly, this technique is unsuitable for commercial practice.

In an attempt to obtain a terephthalic acid suspension having a reduced impurity content from an impurity-containing suspension of terephthalic acid particles in a mother liquor containing a lower aliphatic carboxylic acid solvent without the aforesaid troubles, a method was suggested in British Patent Specification No. 970,492 which comprises feeding a fresh and hot lower fatty acid carboxylic acid solvent to the hot impurity-containing suspension, feeding the resultant mixture to a liquid cyclone, treating the mixture by the cyclone at an elevated temperature, withdrawing an impurity-containing liquid composed mainly of said mother liquor (overflow) from a withdrawal opening provided near one end of the cyclone, and withdrawing a suspension of terephthalic acid particles in a lower aliphatic carboxylic acid solvent consisting mainly of said fresh solvent (underflow) from an opening provided at the other end of the cyclone.

According to this suggestion, a multi-stage liquid cyclone composed of a plurality of, for example four, conventional cyclones in series are employed. Each of the cyclone units include an opening at one end for withdrawing the impurity-containing mother liquor and at the other end an opening for withdrawing the suspension of terephthalic acid and the mixture-feeding opening provided at a suitable position between the two ends.

The inventor of the present application, however, found that in addition to the disadvantage of requiring a plurality of liquid cyclone units, this multi-stage liquid cyclone is extremely difficult to operate with a good balance and good stability in a steady state. When in an attempt to overcome this difficulty, the removal of the impurity-containing mother liquor from the mother liquor-withdrawing opening is improved by using one unit liquid cyclone, the concentration of the suspended solid in the suspension withdrawn from the suspension-withdrawing opening inevitably increases. Hence, the withdrawing openings tend to be clogged. To avoid this trouble, the amount of the fresh and hot lower aliphatic carboxylic acid solvent to be supplied to the hot impurity-containing suspension of terephthalic acid in the mother liquor containing the lower aliphatic carboxylic acid solvent must be unduly increased, and this results in a failure of the operation. Even if the amount of the fresh solvent is increased to an extent that can still render the operation possible, it is impossible to achieve a satisfactory effect of removing the impurities. Thus, the multi-stage liquid cyclone method has been found to be essential.

The present inventor continued his work in attempt to remove the new technical defects associated with the use of a liquid cyclone. The work has led to the discovery that the new technical defects can be altogether removed, and a terephthalic acid suspension having a satisfactory reduced impurity content can be obtained by using only one liquid cyclone without the need to use a multistage liquid cyclone system, by feeding a fresh and hot lower aliphatic carboxylic acid solvent to a hot impurity-containing suspension of terephthalic acid in a mother liquor containing a lower aliphatic carboxylic acid solvent, feeding the resulting mixture into a liquid cyclone, and additionally feeding a fresh lower aliphatic carboxylic acid solvent (side flow) from a feed opening which is provided in the liquid cyclone at a point between a position apart from an opening from which to withdraw the treated suspension toward the mixture-feeding opening by a distance corresponding to about two-thirds, preferably about one-seconds, of the distance ($h_o$) from the mixture-feeding opening to the suspension-withdrawing opening and a position located apart from the withdrawing opening toward the mixture-feeding opening by a distance corresponding to about one-tenth of the distance ($h_o$).

It has also been found that the operation can be performed with good balance and stability and in a satisfactory steady state, and a good improvement can be achieved both in regard to equipment and operation.

It has also been found that the aforesaid various improvements can be achieved without the need to increase the amount of the fresh solvent further, but by utilizing a part of the fresh and hot lower aliphatic carboxylic acid solvent to be fed to the hot impurity-containing suspension of terephthalic acid particles in the mother liquor as the additional fresh solvent.

It has not yet been known by what mechanism the above improvements can be achieved by merely attaching minor modifications in design to the liquid cyclone. The excellent technical progress of the present invention will be readily understood from a comparative study of Examples and Comparative Examples to be given hereinbelow.

It is an object of this invention therefore to provide an improved process for treatment by a liquid cyclone for the recovery of a terephthalic acid suspension having a reduced impurity content.

Figure 2:
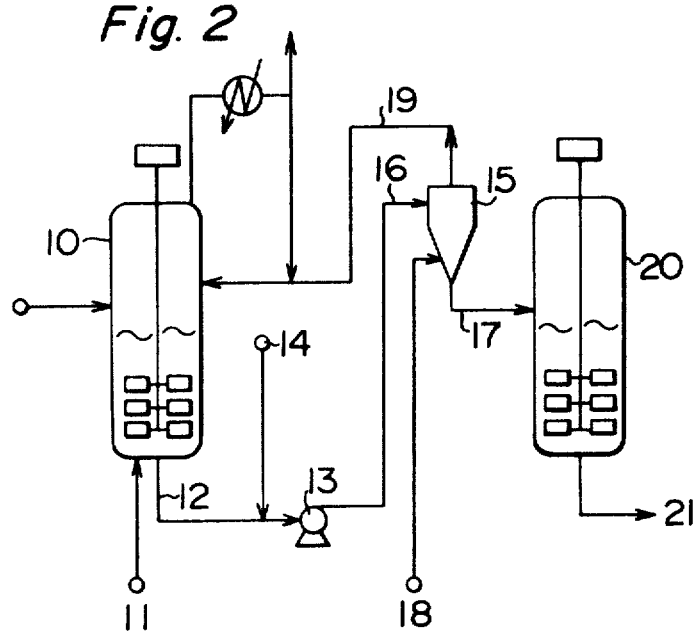

The above and other objects and advantages of the present invention will become more apparent from the following description taken in conjunction with the accompanying drawings in which:

FIG. 1 is a schematic longitudinal sectional view showing one example of a liquid cyclone suitable for the practice of the process of this invention; and FIG. 2 is a schematic flowsheet showing one example of the process of this invention.

The material to be treated by the process of this invention is a liquid-phase catalytic oxidation product of a p-alkylbenzene, or a hot impurity-containing suspension of terephthalic acid particles in a mother liquor containing a lower aliphatic carboxylic acid solvent which is derived from the above oxidation product. The material can be an oxidation product which is obtained by catalytically oxidizing a p-alkylbenzene such as p-xylene in the liquid phase with a molecular oxygen-containing gas such as air in a lower aliphatic carboxylic acid solvent such as acetic acid in the presence of a heavy metal-containing oxidation catalyst at an elevated temperature (e.g., about 170 to about 240° C.) and an elevated pressure (e.g., about 9 to about 28 Kg/cm$^2$·G); or a product obtained by subjecting the oxidation product to various known purifying treatments in various solvents such as hydrogenation, decarbonylation, oxidation, recrystallization or high-temperature dipping.

The solvent used at the time of purification are solvents inert to terephthalic acid, for example, lower aliphatic carboxylic acids such as acetic acid and propionic acid; water; and ketones such as acetone and methyl ethyl ketone. Of these, acetic acid, water, or a mixture of acetic acid and water is especially suitable.

The liquid-phase catalytic oxidation products of p-dialkylbenzenes, and the hot impurity-containing suspensions of terephthalic acid particles in a mother liquor containing a lower aliphatic carboxylic acid solvent contain various impurities. For example, the former contains oxidation intermediates (e.g., 4-carboxybenzaldehyde), colored by-products, and the oxidation catalyst as major impurities. The latter contains somewhat decreased amounts of the oxidation intermediates and colored by-products as major impurities and at times the oxidation catalyst although the types of impurities vary depending upon the treating means employed. Furthermore, a part of terephthalic acid is dissolved in these impurity-containing suspensions.

The hot impurity-containing suspension of terephthalic acid particles in a mother liquor containing a lower aliphatic carboxylic acid solvent to be treated preferably has a terephthalic acid particles:mother liquor weight ratio of 1.5:1 to 10:1, preferably about 3:1 to about 8:1.

A fresh and hot lower aliphatic carboxylic acid solvent is fed to the hot impurity-containing suspension.

The resulting mixture is fed into a liquid cyclone, and treated in it at an elevated temperature. The temperature of the hot suspension containing impurities is equal to the temperature for the oxidation reaction, or lower than it by not more than 50° C. Preferably, the fresh and hot lower aliphatic carboxylic acid solvent is supplied at a temperature which is up to about 50° C. higher or lower than the temperature of the hot impurity-containing suspension. The suitable amount of the fresh and hot lower aliphatic carboxylic acid solvent to be fed is about 30 to 200% by weight, preferably about 50 to about 150% by weight.

The rate at which the resulting mixture is fed into the mixture-feeding opening of the liquid cyclone can be varied as desired. Preferably, it is about 1 to 20 m/sec (in terms of a linear velocity), more preferably about 3 to about 10 m/sec. As is conventional, the mixture is conveniently fed into the liquid cyclone along the direction of the turning of the terephthalic acid suspension in the liquid cyclone so that it may not counteract the turning flow of the suspension.

In the process of this invention, the mixture is fed into the liquid cyclone in the aforesaid manner, and treated in it at a temperature lower or higher than the oxidation reaction temperature by not more than 50° C., preferably not more than 30° C. A liquid containing impurities which consists mainly of the above mother liquor is taken out from the mother liquor withdrawing opening provided near one end of the cyclone. In the meantime, the suspension of terephthalic acid particles in the lower aliphatic carboxylic acid solvent composed mainly of the above fresh solvent is withdrawn from the suspension-withdrawing opening provided near the other end of the cyclone.

The most important characteristic of the process of this invention is to feed an additional supply of fresh lower aliphatic carboxylic acid solvent through an opening located between a position apart from the suspension-withdrawing opening toward mixture-feeding opening by a distance corresponding to about two-thirds, preferably about one-second, of the distance ($h_o$) from the mixture-feeding opening to the suspension-withdrawing opening of the liquid cyclone and a position apart from the suspension-withdrawing opening toward the mixture-feeding opening by a distance corresponding to about one-tenth of the distance ($h_o$).

If the feeding of an additional supply of fresh lower aliphatic carboxylic acid solvent is omitted, the improvements intended by the present invention cannot be achieved even when the lower aliphatic carboxylic acid solvent in an amount corresponding to the total amount of the fresh and hot lower aliphatic carboxylic acid solvent and the additional supply of fresh lower aliphatic carboxylic acid solvent is used for the formation of the above mixture. This is shown in Comparative Example 2 given hereinbelow. Furthermore, as shown in Comparative Example 1 below, the improvements intended by the invention cannot be achieved when an additional supply of fresh solvent is fed at a position spaced apart from the suspension withdrawal opening by a distance exceeding $h_o \times \frac{2}{3}$.

It is usual that the fresh and hot solvent used to form the above mixture and the additional fresh solvent are the same as the lower aliphatic carboxylic acid solvent contained as a main component in the mother liquor of the hot impurity-containing suspension. But they may be different. Furthermore, the fresh and hot solvent for forming the mixture may be different from the additional fresh solvent.

Preferably, as is the case with the supply of the mixture to the cyclone, the additional fresh solvent is fed along the direction of the turning flow of the terephthalic acid suspension within the liquid cyclone. The amount of the additional fresh solvent is, for example, about 5 to about 100% by weight, preferably about 10 to about 50% by weight, based on the weight of the mixture fed into the cyclone through the mixture-supplying opening. If the amount of the additional fresh solvent is too small, there is a tendency that a sufficient effect is difficult to obtain. Larger amounts than the specified range do not give a correspondingly increased effect. Hence, the amount should be selected from the above-exemplified range.

It is preferred to feed the additional fresh solvent in the hot state as is the case with the fresh and hot solvent for forming the mixture. Preferably, the solvent is heated at a temperature which is up to about 50° C. higher or lower than the temperature of the hot impurity-containing suspension. It does not need to be the same temperature as the fresh and hot solvent for the formation of the mixture.

The linear speed of feeding the additional fresh solvent preferably be not more than about 3 times, for example about 0.3 to 3 times, that of feeding the mixture to be fed into the mixture-feeding opening.

Since the terephthalic acid suspension thus obtained by the process of this invention has a sufficiently reduced impurity content, it can be subjected to a post-treatment without any further similar treatment. For example, it is sent to a subsequent purifying tank without lowering its temperature to any great extent, at which it is purified. Then, by a customary method, high purity terephthalic acid can be separated.

By treatment of a hot impurity-containing suspension of terephthalic acid particles in a mother liquor containing a lower aliphatic carboxylic acid solvent in a single liquid cyclone in accordance with this invention, the ratio of replacement of the impurity-containing mother liquor by the fresh solvent can be increased to 80 to 95% by weight.

The ratio of replacement, as referred to herein, is the value obtained by subtracting the ratio of the remaining mother liquor (wt.%; see the footnote to Table 1) from 100 (wt.%).

One embodiment of the process of this invention is described in more detail below by refering to FIGS. 1 and 2.

In FIG. 1, a liquid-phase catalytic oxidation product of a p-alkylbenzene (e.g., p-xylene), or a hot, impurity-containing suspension of terephthalic acid particles in a mother liquor containing a lower aliphatic carboxylic acid solvent which is taken out from a purifying device is fed as a mixture with a newly fed fresh and hot lower aliphatic carboxylic acid solvent into a cylindrical part 2 of a liquid cyclone through an opening 4. Preferably, the mixture is fed along the direction of the turning flow of the terephthalic acid suspension within the cyclone, specifically along the circumberential direction across the cylindrical part 2. An additional supply of a fresh solvent, preferably heated, is fed into a conical part 1 of the liquid cyclone through an opening 9 preferably along the direction of the turning flow of the terepthalic acid suspension within the liquid cyclone.

At this time, the feeding of the additional supply of the fresh lower aliphatic carboxylic acid solvent is effected between a point (Ha) which is located apart from an opening 7 for withdrawal of the suspension toward the supply opening 4 by a distance corresponding to about two-thirds of the distance ($h_o$) from the opening 4 to the opening 7 and a position (Hb) which is located apart from the opening 7 toward the opening 4 by a distance corresponding to about one-tenth of the distance $h_o$. FIG. 1 shows an embodiment in which the additional fresh solvent is fed at a position apart from the opening 7 toward the opening 4 by the distance $h_1$.

As a result of this treatment with the liquid cyclone, an impurity-containing liquid composed mainly of the aforesaid mother liquor is taken out from an opening 6 which is made up of an overflooding pipe 5 with a markedly improved efficiency. In the meantime, as a result of replacement of the mother liquor by the fresh solvent, a suspension of terephthalic acid particles in the lower aliphatic carboxylic acid solvent composed mainly of the fresh solvent (denoting both the fresh and hot solvent used to form the aforesaid mixture and the additional fresh solvent) is withdrawn from a pipe 8 through an opening 7.

The following examples specifically illustrate the process of this invention. These examples used an apparatus including a reactor 10 for the catalytic oxidation of p-xylene, a pump 13 for feeding a hot, impurity-containing suspension of terephthalic acid, a liquid cyclone 15, and a receiver tank 20 for a suspension of terephthalic acid having a reduced impurity content after separation of the mother liquor by replacement with a solvent.

EXAMPLE 1

The apparatus shown in FIG. 2 was used. In oxidation reactor 10, p-xylene was continuously oxidized in acetic acid in the presence of a catalyst comprising cobalt, manganese and bromine at 190° C. and 11 kg/cm$^2$·G while feeding air from an air supply line 11. The resulting impurity-containing suspension of terephthalic acid in a mother liquor containing acetic acid (the weight ratio of the mother liquor to terephthalic acid was 2.6; and the total concentration of cobalt and manganese in the mother liquor was $2.8 \times 10^{-2}$ gram-ion/kg) was continuously withdrawn from a line 12 at the bottom of oxidation reactor 10 at a rate of 1,250 kg/hr. Acetic acid heated at 180° C. was fed into the terephthalic acid suspension at a rate of 1,050 kg/hr from a line 14. The resulting mixture (the weight ratio of the mother liquor to the terephthalic acid was 5.6; and the total concentration of cobalt and manganese was $1.29 \times 10^{-2}$ gram-ion/kg) was continuously fed into the cylindrical portion of a liquid cyclone 15 in the tangential direction at a rate of 2,300 kg/hr from a line 16. The linear speed of the mixture fed to the cyclone was adjusted to 3.7 m/sec at the supply opening, and the temperature of the inside of the liquid cyclone was maintained at 180° C. From an opening 18 on the side of liquid cyclone 15, acetic acid heated at 180° C. was fed continuously in the tangential direction at a rate of 400 kg/hr (corresponding to 17% by weight based on the mixture fed into the liquid cyclone). The linear speed of the additional acetic acid fed at this time was 1.88 times as large as that of the mixture fed into the liquid cyclone. The position of feeding the additional acetic acid into the liquid cyclone 15 was at a hight ($h_1$) of about 0.24 $h_o$ from the bottom 7 of the liquid cyclone (see FIG. 1).

A suspension of terephthalic acid in acetic acid having a reduced impurity content (the weight ratio of the acetic acid mother liquor to terephthalic acid was 2.0, and the total concentration of cobalt and manganese in the acetic acid mother liquor was $0.66 \times 10^{-2}$ gram-ion/kg) was withdrawn at a rate of 975 kg/hr from a line 17 at the bottom of the liquid cyclone. The ratio of recovery of terephthalic acid was 93%. The ratio of replacement of the impurity-containing mother liquor in the acetic acid suspension of terephthalic acid obtained from the line 17, calculated from the concentration of the catalyst in the mixture, was 49% by weight based on the mixture. The ratio of the impurity-containing mother liquor remaining in the terephthalic acid suspension withdrawn through line 17 was 17% by weight based on the mother liquor of the liquid-phase oxidation product withdrawn from line 12.

The results are shown in Table 1.

EXAMPLE 2

Example 1 as repeated except that the amount of the terephthalic acid suspension to be withdrawn from line 17 at the bottom of the liquid cyclone was adjusted to 700 kg/hr, and accordingly the amount of the mother liquor withdrawn from line 19 was increased. The ratio of recovery of terephthalic acid was 86%. The ratio of replacement of the impurity-containing mother liquor in the acetic acid suspension of terephthalic acid withdrawn from line 17 was 63% by weight based on the mixture. The ratio of the remaining impurity-containing mother liquor contained in the acetic acid suspension of terephthalic acid withdrawn from line 17 was 8% by weight based on the mother liquor of the liquid-phase oxidation product withdrawn from line 12. Despite the increase of the degree of concentration of the terephthalic acid suspension from line 17, the operation of the liquid cyclone was stable, and could be performed in a steady state for long periods of time.

The results are shown in Table 1.

COMPARATIVE EXAMPLE 1

Example 1 was repeated except that the opening 9 was in a position corresponding to $0.71 \times h_o$ and that the amount of terephthalic acid suspension withdrawn was slightly varied within the range of error of the operation. The results are shown in Table 1.

COMPARATIVE EXAMPLE 2

Example 1 was repeated except that no additional fresh acetic acid was fed into the cyclone, and the amount of fresh and hot acetic acid to be fed into the liquid-phase reaction product from line 14 was made equal to the total amount of the fresh and hot acetic acid and the additional fresh acetic acid used in Example 1. The results are shown in Table 1.

Table 1

|  | Example | | Comparative Example | |
|---|---|---|---|---|
|  | 1 | 2 | 1 | 2 |
| Amount of the starting mixture fed (kg/hr) | 2300 | 2300 | 2300 | 2700 |
| Linear speed of feeding the starting mixture (m/sec.) | 3.7 | 3.7 | 3.7 | 4.3 |

Table 1-continued

| | Example | | Comparative Example | |
|---|---|---|---|---|
| | 1 | 2 | 1 | 2 |
| Operating temperature (°C.) | 180 | 180 | 180 | 180 |
| Position of feeding the additional acetic acid ($h_1$) (*1) | 0.24ho | 0.24ho | 0.71ho | — |
| Ratio of additional acetic acid fed (*2) | 0.17 | 0.17 | 0.17 | 0 |
| Ratio of the linear speed of feeding the additional acetic acid (*3) | 1.88 | 1.88 | 1.88 | — |
| Amount of the terephthalic acid suspension withdrawn (kg/hr) | 975 | 700 | 970 | 975 |
| Ratio of recovery of terephthalic acid (%) (*4) | 93 | 86 | 93 | 90 |
| Ratio of replacing the mother liquor (%) (*5) | 49 | 63 | 19 | 0 |
| Ratio of the remaining mother liquor (%) (*6) | 17 | 8 | 27 | 28 |
| Ratio of replacement of the impurity-containing mother liquor by solvent (%) | 83 | 92 | 73 | 72 |

(*1) See FIG. 1.
(*2) The weight ratio of the additional fresh acetic acid to the starting mixture to be fed into the liquid cyclone.
(*3) The ratio of the linear speed of feeding the starting mixture into the liquid cyclone to that of feeding the additional fresh acetic acid.
(*4) The ratio of recovery of terephthalic acid from the suspension withdrawn from the liquid cyclone based on terephthalic acid in the oxidation product withdrawn from the oxidation reactor.
(*5) The ratio of replacement of the mother liquor in the acetic acid suspension of terephthalic acid withdrawn from line 17 based on the starting mixture fed into the liquid cyclone by line 16.
(*6) The ratio of the remaining impurity-containing mother liquor contained in the acetic acid suspension of terephthalic acid in line 17 based on the oxidation product withdrawn from the reactor through line 12.

What we claim is:

1. A process for treatment by a liquid cyclone for the production of a suspension of terephthalic acid having a reduced impurity content which comprises supplying a fresh and hot lower aliphatic carboxylic acid solvent to a liquid-phase catalytic oxidation product of a p-alkylbenzene or a hot, impurity-containing suspension of terephthalic acid particles in a mother liquor containing a lower aliphatic carboxylic acid solvent, feeding the resulting mixture into a liquid cyclone, treating it in the cyclone at an elevated temperature, withdrawing an impurity-containing liquid composed mainly of said mother liquor from a withdrawal opening provided near one end of the cyclone, and withdrawing a suspension of terephthalic acid particles in a lower aliphatic carboxylic acid solvent consisting mainly of said fresh solvent from a withdrawal opening provided near the other end of the cyclone; wherein a fresh lower aliphatic carboxylic acid solvent is additionally supplied into the cyclone through an opening provided between a position apart from the suspension withdrawal opening of the liquid cyclone toward its mixture-feeding opening by a distance corresponding to about two-thirds of the distance ($h_o$) from the mixture-feeding opening to the suspension withdrawal opening and a position apart from the suspension withdrawal opening toward its mixture feeding opening by a distance corresponding to about one-tenth of the distance ($h_o$).

2. The process of claim 1 wherein the additional fresh solvent is fed along the direction of the turning flow of the terephthalic acid suspension within the liquid cyclone.

3. The process of claim 1 wherein the linear speed of feeding the additional fresh solvent is about 0.3 to about 3 times as large as that of feeding the mixture into the feed opening.

4. The process of claim 1 wherein the amount of the additional fresh solvent is about 10 to about 50% by weight based on the weight of the mixture to be fed into the cyclone.

5. The process of claim 1 wherein the fresh solvent first added to the oxidation product and the additionally supplied fresh solvent are heated at a temperature which is up to about 50° C. higher or lower than the temperature of the hot impurity-containing suspension.

* * * * *